US008178748B2

(12) United States Patent
Hammons et al.

(10) Patent No.: US 8,178,748 B2
(45) Date of Patent: May 15, 2012

(54) ABSORBENT ARTICLE

(75) Inventors: John Lee Hammons, Hamilton, OH (US); Robert Ya-lin Pan, Symmes Township, OH (US); Brent Taylor Ginn, Monroe, OH (US); Brian Francis Gray, Cincinnati, OH (US); Casandre Maffett Walsh, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 730 days.

(21) Appl. No.: 12/032,182

(22) Filed: Feb. 15, 2008

(65) Prior Publication Data
US 2009/0209930 A1   Aug. 20, 2009

(51) Int. Cl.
  *A61F 13/15*   (2006.01)
  *A61F 13/20*   (2006.01)
(52) U.S. Cl. .................................. 604/378; 604/385.04
(58) Field of Classification Search .................. 604/378, 604/385.04; 424/402; 428/131
  See application file for complete search history.

(56) References Cited

U.S. PATENT DOCUMENTS

| | | | |
|---|---|---|---|
| 5,415,640 A | 5/1995 | Kirby et al. | |
| 5,533,991 A | 7/1996 | Kirby et al. | |
| 5,755,710 A | 5/1998 | Menard | |
| 6,117,523 A | 9/2000 | Sugahara | |
| 6,436,080 B1 * | 8/2002 | Carlucci et al. | 604/385.01 |
| 6,461,339 B1 | 10/2002 | Sugahara | |
| 6,465,711 B1 | 10/2002 | Brisebois | |
| 6,911,574 B1 | 6/2005 | Mizutani | |
| 6,960,349 B2 * | 11/2005 | Shantz et al. | 424/402 |
| 7,067,711 B2 | 6/2006 | Kuroda et al. | |
| 7,090,665 B2 * | 8/2006 | Ohashi et al. | 604/385.14 |
| 2002/0123729 A1 | 9/2002 | Bewick-Sonntag et al. | |
| 2003/0060792 A1 * | 3/2003 | Harriz et al. | 604/385.04 |
| 2004/0161402 A1 * | 8/2004 | Brooks et al. | 424/70.15 |
| 2006/0243406 A1 * | 11/2006 | Shannon et al. | 162/158 |

FOREIGN PATENT DOCUMENTS

| | | |
|---|---|---|
| EP | 1 022 007 B1 | 3/2006 |
| WO | WO 93/12745 | 7/1993 |

OTHER PUBLICATIONS

PCT International Search Report dated Apr. 6, 2009.

* cited by examiner

*Primary Examiner* — Melanie Hand
(74) *Attorney, Agent, or Firm* — Amanda T. Barry; Gary J. Foose

(57) ABSTRACT

An absorbent article for wearing in an undergarment. The absorbent article can include a nonwoven. The nonwoven can have a nonwoven body facing surface. The nonwoven can have a main body portion and pair of spaced apart flaps associated with the main body portion. Part of the main body portion can have a hydrophilic zone that is more hydrophilic than a portion of the flaps. The absorbent article can have film having a film garment facing surface wherein at least part of the film garment facing surface faces the nonwoven body facing surface.

20 Claims, 6 Drawing Sheets

ABSORBENT ARTICLE

FIELD OF THE INVENTION

This invention relates to absorbent articles designed to be worn in the crotch of the wearer.

BACKGROUND OF THE INVENTION

Absorbent articles designed to be worn in the crotch of the wearer, including sanitary napkins, pantiliners, and the like, can be used to collect discharges from a woman's vagina or urethra. Many absorbent articles include flaps. Generally, the flaps extend laterally from a main body and are intended to be folded around the edges of the wearer's panties in the crotch region. Thus, the flaps are disposed between the edges of the wearer's panties in the crotch region and the wearer's thighs. Commonly, the flaps are provided with an attachment means for affixing the flaps to the underside of the wearer's panties.

The body facing surface of an absorbent article typically comprises a topsheet. For an absorbent article having flaps, the topsheet of the absorbent article can be thought of as having two portions having functions that differ from one another. Part of the main body portion of the topsheet, i.e. that portion of the topsheet part of which is generally aligned along the longitudinal centerline of the absorbent article, can provide for fluid acquisition and retention. The flaps can help stabilize the napkin from shifting out of place and in some embodiments may help reduce soiling of the wearer's body, undergarments, and outer clothing.

Portions of the topsheet are likely to be in contact with the wearer's body during use. For example, as the absorbent article is worn, the topsheet may contact the labia and surrounding tissue. If the absorbent article has flaps, when the flaps are folded around the edges of the wearer's panty, the topsheet of the absorbent article may contact the surfaces of the wearer's inner thighs. Irritation of the skin can develop at these contact locations if the materials forming the topsheet do not have a soft surface texture and sufficient flexibility or other materials forming the absorbent article are not sufficiently flexible.

Apertured films are widely recognized as providing for topsheets having outstanding fluid handling characteristics, including high rates of fluid acquisition, limited rewet, and limited lateral spreading. Softness of apertured films can be provided for by imparting surface texture to the film. ALWAYS sanitary napkins, marketed by the Procter & Gamble Co., Cincinnati, Ohio, employ an apertured film topsheet known in the trade as DRI-WEAVE. One drawback to film topsheets is that film topsheets can be more expensive than available alternatives, such as nonwoven materials.

Nonwoven materials can also be employed as the topsheet of an absorbent article. Nonwoven topsheets are thought to provide for a soft body contacting surface and have acceptable fluid handling characteristics. Although nonwoven topsheets tend to be inexpensive relative to available alternatives, nonwoven topsheets may not be without performance limitations. One problem associated with absorbent articles having a nonwoven topsheet and flaps is that fluid collected by topsheet tends to spread laterally within the nonwoven layer. In typical absorbent articles having flaps, there is little or no absorbent capacity in the flaps because the absorbent core typically does not extend to the flaps. Thus, fluid that spreads to the flaps is not drawn more deeply into the absorbent article, which results in soiled wings. Soiled wings can be visually unattractive to the wearer and can contribute to soiling of the wearer's body, undergarments, and outer clothing.

For most absorbent articles, the topsheet is comprised of a single material across the entire body facing surface of the absorbent article. That is, the body facing surface of the flaps is the same as the body facing surface of the main body of the absorbent article. Such a design makes the absorbent article easy to produce because only one web of material needs to be handled during manufacture to form the body facing layer of the absorbent article and fewer bonding locations may be needed to secure the topsheet to the other materials constituting the absorbent article. One limitation of such a design is that the different functional aspects of different parts of the absorbent article, such as the main body portion and the flaps, may be inadequately addressed in such a simple design. Another limitation of such a design is that the design of the body facing surface of the absorbent article may not be as cost effective as desirable, particularly if a relatively expensive material is used to form the entire body facing surface of the absorbent article.

With these limitations in mind, there is a present unaddressed need for an absorbent article in which the materials comprising the body facing surface of the absorbent article are arranged such that the different portions of the body facing surface of the absorbent article deliver the desired function and have the desired attributes. There is a further unaddressed need for an absorbent article in which materials comprising the body facing surface of the absorbent article are selected and arranged to provide for cost effective production.

SUMMARY OF THE INVENTION

An absorbent article for wearing in an undergarment is disclosed. The absorbent article can comprise a nonwoven having a nonwoven body facing surface and a nonwoven garment facing surface. The nonwoven can comprise a main body portion. The main body portion can have two spaced apart longitudinal side edges, two spaced apart transverse edges, and a longitudinal centerline. The nonwoven can further comprises a pair of spaced apart flaps associated with the main body portion. The flaps can be sized and dimensioned for folding around and securing to the wearer's undergarment. Each of the flaps can be associated with the main body portion at a juncture. One flap can extend laterally outward from each of the longitudinal side edges. Part of the main body portion can comprise a hydrophilic zone that is more hydrophilic than a portion of the flaps. The absorbent article can further comprise an apertured film having a film body facing surface and a film garment facing surface. At least part of the film garment facing surface can face the nonwoven body facing surface of the main body portion.

DETAILED DESCRIPTION OF THE INVENTION

Figure 1:
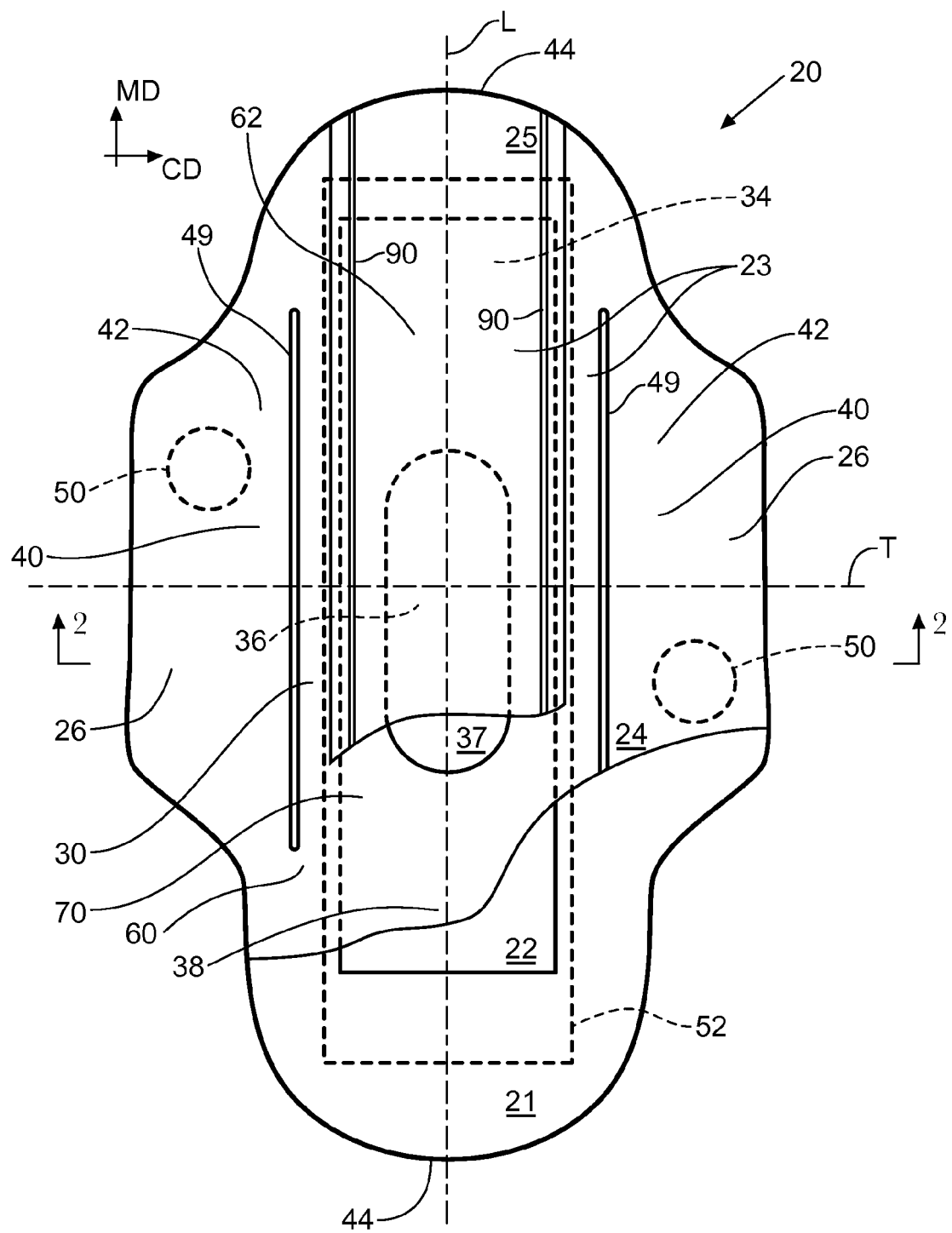
FIG. 1 is a top view of an absorbent article.

As used herein, the term "nonwoven" refers to a web having a structure of individual fibers or threads which are interlaid, but not in a regular, repeating manner as in a woven or knitted fabric. Nonwoven webs or fabrics can be formed using many processes, such as, for example, meltblowing processes, spunbonding processes, hydroentangling processes, and bonded carded web processes. The basis weight of nonwoven fabrics is usually expressed in grams per square meter (gsm) and the fiber diameters are usually expressed in microns. Fiber size can also be expressed in denier. Nonwoven materials having a basis weight between about 10 gsm to about 200 gsm can be practical for use in absorbent articles.

The constituent fibers of nonwoven webs can be polymer fibers, and can be monocomponent, bicomponent, and/or biconstituent, capillary channel fibers, and can have major cross-sectional dimensions (e.g., diameter for round fibers) ranging from 5-200 microns. The constituent fibers can range from about 0.1 denier to about 100 denier.

As used herein, "spunbond fibers" refers to small diameter fibers that are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 10 and about 40 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

As used herein, the term "capillary channel fibers" refers to fibers having capillary channels capable of facilitating fluid movement via capillarity. Such fibers can be hollow fibers, for example, but are preferably fibers having capillary channels on their outer surfaces. The capillary channels can be of various cross-sectional shapes such as "U-shaped," "H-shaped," "C-shaped," and "V-shaped."

As used herein, the term "joined" refers to the condition in which a first member is attached or connected to a second member either directly or indirectly. The term "joined" also refers to the condition in which the first member is attached or connected to an intermediate member which in turn is attached, or connected to the second member.

An absorbent article 20 for wearing in an undergarment is shown in FIG. 1. The absorbent article 20, and components thereof, can have a machine direction MD and a cross machine direction CD. The machine direction can coincide with the longitudinal centerline L and the cross direction CD can coincide with the transverse centerline T. As shown in FIG. 1, the absorbent article 20 can comprise a backsheet 21, an absorbent core 22, and topsheet 23. The topsheet 23 can be comprised of a nonwoven 24 and an apertured film 25. The nonwoven 24 can be between the apertured film 25 and the absorbent core 22. The nonwoven 24 can have a pair of flaps 26. The nonwoven 24 has a longitudinal centerline L and a transverse centerline T. The term "longitudinal", as used herein, refers to a line, axis or direction in the plane of the nonwoven 24 that is generally aligned with (e.g., approximately parallel to) a vertical plane which bisects a standing wearer into left and right body halves when the absorbent article 20 is worn. The term "transverse" refers to a line, axis or direction that generally lies within the plane of the nonwoven 24 that is generally perpendicular to the longitudinal direction. The longitudinal centerline L can be oriented in the longest dimension of the absorbent article 20 and the transverse centerline T can be orthogonal thereto.

The nonwoven 24 has a main body portion 30 and can have a pair of flaps 26 associated therewith. The main body portion 30 of nonwoven 24 has two spaced apart longitudinal side edges 42 and two spaced apart transverse edges 44. The main body portion 30 of nonwoven 24 has a front region 34, a back region 38, and a central region 36 disposed between the front region 34 and back region 38. The front region 34, central region 36, and back region 38 are generally disposed along the longitudinal centerline L of the nonwoven 24 and generally divide the main body portion 30 of the nonwoven 24 into thirds along longitudinal centerline L. The front region 34, central region 36, and back region 38 lie within the plane of the nonwoven 24 defined by the longitudinal centerline L and transverse centerline T.

Each of the flaps 26 is associated with the main body portion 30 at a juncture 40. One flap 26 extends laterally outward, in a direction away from the longitudinal centerline L, from each of the longitudinal side edges 42. The flaps 26 can extend laterally outward from each longitudinal side edge 42 of the central region 36. The juncture 40 can be a straight line, a curved line, or a combination of straight and curved lines, along which a flap 26 is associated with the main body portion 30 of nonwoven 24. The juncture 40 can be a curve that is concave (i.e. opens in a direction away from the longitudinal centerline L) relative to the longitudinal centerline L of the main body portion 30 of nonwoven 24.

The nonwoven 24 has a nonwoven body facing surface 60 and a nonwoven garment facing surface. The nonwoven body facing surface 60 is the surface of the nonwoven 24 for which the surface of the main body portion 30 of the nonwoven 24 is oriented towards the wearer's body when the absorbent article 20 is in use. The nonwoven garment facing surface is the surface of the nonwoven 24 for which the surface of the main body portion 30 of the nonwoven 24 between the longitudinal side edges 42 of the nonwoven 24 is oriented away from the wearer's body (in other words, towards the wearer's undergarment) when the absorbent article 20 is in use.

Apertured film 25 has an apertured film body facing surface 62 and an apertured film garment facing surface. The apertured film body facing surface 62 is the surface of the apertured film 25 oriented towards the wearer's body when the absorbent article 20 is in use. The apertured film garment facing surface is the surface of the apertured film 25 oriented away from the wearer's body (in other words, towards the wearer's undergarment) when the absorbent article 20 is in use. At least part of the apertured film 25 garment facing surface faces the nonwoven body facing surface 60 of the main body portion 30 of the nonwoven 24. The apertured film 25 can be joined to the nonwoven body facing surface 60 of the main body portion 30 of nonwoven 24 such that the apertured film garment facing surface is in contacting relationship with the nonwoven body facing surface 60. The apertured film 25 can be joined to the nonwoven 24 by a method selected from the group consisting of ultrasonic bonding, fusion bonding, adhesive bonding, and combinations thereof or any other method known in the art for joining elements in absorbent articles. The apertured film 25 can be joined to the nonwoven 24 along a pair of bonding lines 90. Each bonding line 90 can be between the hydrophilic zone 37 and a flap 26. The bonding lines can be straight lines, curved lines, or lines comprising both straight and curved portions.

The absorbent article can further comprise a flap adhesive 50 and a central adhesive 52, each of which is applied to the garment facing surface of the backsheet 21 of the absorbent article 20. The flap adhesive 50 can be operatively positioned, sized, and dimensioned to attach a flap 26 to the wearer's panty. The central adhesive 52 can be operatively positioned, sized, and dimensioned to attach a portion of the absorbent article 20 coordinated with the longitudinal centerline L to the wearer's panty.

The absorbent article 20 has an absorbent article body facing surface 70 and an absorbent article garment facing surface. Similarly, each component of the absorbent article, including the absorbent core 22 and backsheet 21, has a body facing surface and a garment facing surface associated with each component, the body facing surface and garment facing surfaces of each component identifiable based on the orientation of the material constituting the component that lies between a projection orthogonal to the longitudinal centerline L and transverse centerline T of the longitudinal side edges 42 of the nonwoven 24. That is, the body facing surface and garment facing surface of the absorbent article and components thereof can be identified based on the orientation of the absorbent article or component thereof when the absorbent article is laid flat and the flaps are not folded around the wearer's undergarment or in a folded position.

Part of the main body portion 30 of nonwoven 24 can have a hydrophilic zone 37. The hydrophilic zone 37 can be a portion of nonwoven 24 that is relatively more hydrophilic as compared to a portion of the flaps 26. The hydrophilic zone 37 can be an antifouling zone.

The nonwoven 24 can be comprised of a single unitary homogeneous web such as can be obtained from cutting nonwoven web 24 from homogeneous stock in which the nonwoven web has the same structure throughout (i.e. homogeneous or homogeneous at some scale). The nonwoven web 24 can comprise fibers that are of the same type, size, and geometry and are arranged such that the web is homogeneous, having the same structure, density, and basis weight at all portions thereof. The nonwoven 24 can be a hydrophobic nonwoven. The unaltered or untreated constituent fibers of a portion or all of the nonwoven 24 can have a contact angle with water of less than 90 degrees. A hydrophilic zone 37 can be created in the nonwoven web by treating a portion of the nonwoven 24 with a substance that results in the treated portion of the nonwoven web 24 being more hydrophilic than untreated portions of the nonwoven web 24. The substance can be affixed, permanently or temporarily, to the fibers forming the nonwoven 24. For example, the substance can be coated on, enrobe, and/or partially enrobe the constituent fibers of the nonwoven web 24. The substance can be within the interstitial spaces between fibers constituting the nonwoven 24.

Another option for creating a hydrophilic zone 37 is to use a non-homogeneous stock in which portions of the stock differ from other portions of the stock. For example the fibrous structure of the hydrophilic zone 37 of the nonwoven web 24 can differ from the fibrous structure of parts of the nonwoven web 24 that are not part of the hydrophilic zone in one of several characteristics, including, but not limited to, type of fiber, size of fiber, geometry of fiber, basis weight, and fiber arrangement.

The hydrophilic zone 37 can be integral with the main body portion 30 of nonwoven 24. That is, the hydrophilic nature of the hydrophilic zone 37 can be imparted by the physical and/or chemical makeup of the constituent fibers of the hydrophilic zone 37.

A portion or the entire main body portion 30 of nonwoven 24 can be rendered hydrophilic to form a hydrophilic zone 37 that is coterminous with the main body portion 30 of nonwoven 24. Portions of the nonwoven 24 between the hydrophilic zone 37 and the flaps 26 can be less hydrophilic than the hydrophilic zone.

The nonwoven 24 can further comprise a pair of fusion barriers 49. The fusion barriers 49 can be disposed on opposing sides of the longitudinal centerline L. Each of the fusion barriers 49 can be between the longitudinal centerline L and one of the flaps 26. A fusion barrier 49 can be a portion of the nonwoven wherein the fibers constituting the nonwoven 24 are fused together such that the capillary network between the fibers is substantially altered or destroyed relative to portions of the nonwoven 24 adjacent or away from the fusion barrier 49. A fusion barrier 49 can be formed by compressing, optionally in combination with heat, the nonwoven 24, thereby fusing together the fibers constituting the nonwoven. By substantially altering or destroying the capillary network between fibers of the nonwoven 24 it is thought that a fusion barrier 49 can resist capillary transport of fluid across the fusion barrier 49. By arranging the fusion barriers 49 such that one fusion barrier is between each flap 26 and the longitudinal centerline L, it is thought that the potential for fluid to migrate from the main body portion 30 to the flaps 26 can be reduced. The fusion barriers 49 can be positioned laterally in-board of the longitudinal side edges 42 such that a fusion barrier 49 is between each flap 26 and the hydrophilic zone 37.

Figure 2:
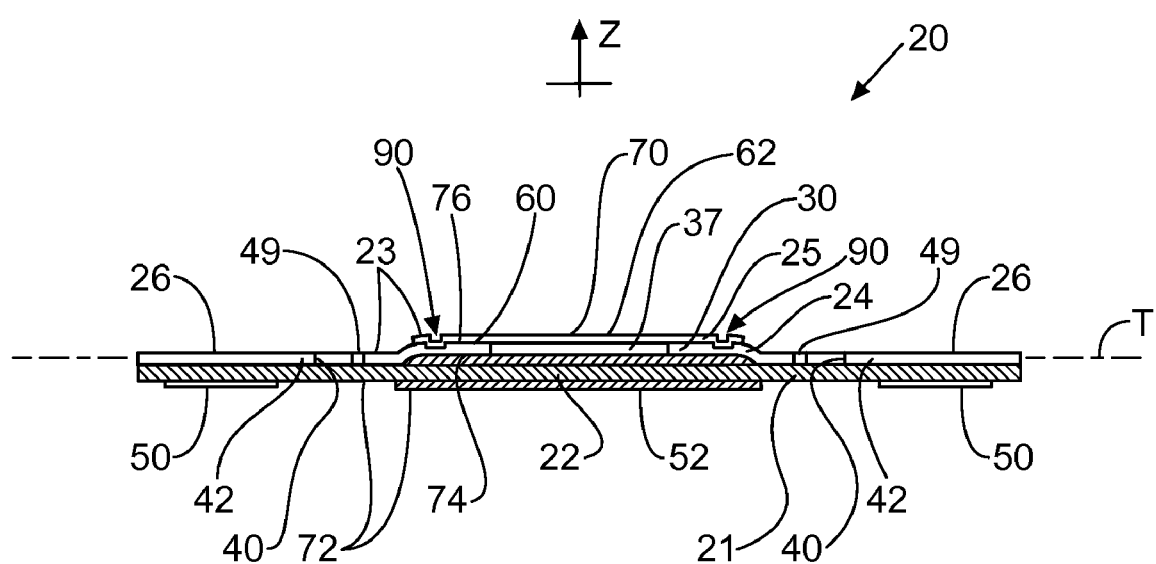
FIG. 2 is a cross section of an absorbent article as marked in FIG. 1.

A cross section of FIG. 1 is illustrated in FIG. 2, in which the absorbent article garment facing surface 72, nonwoven garment facing surface 74, and apertured film garment facing surface 76 are illustrated. The absorbent article 20 can have a Z direction out of plane of the plane defined by the longitudinal centerline L and transverse centerline T.

Figure 3:
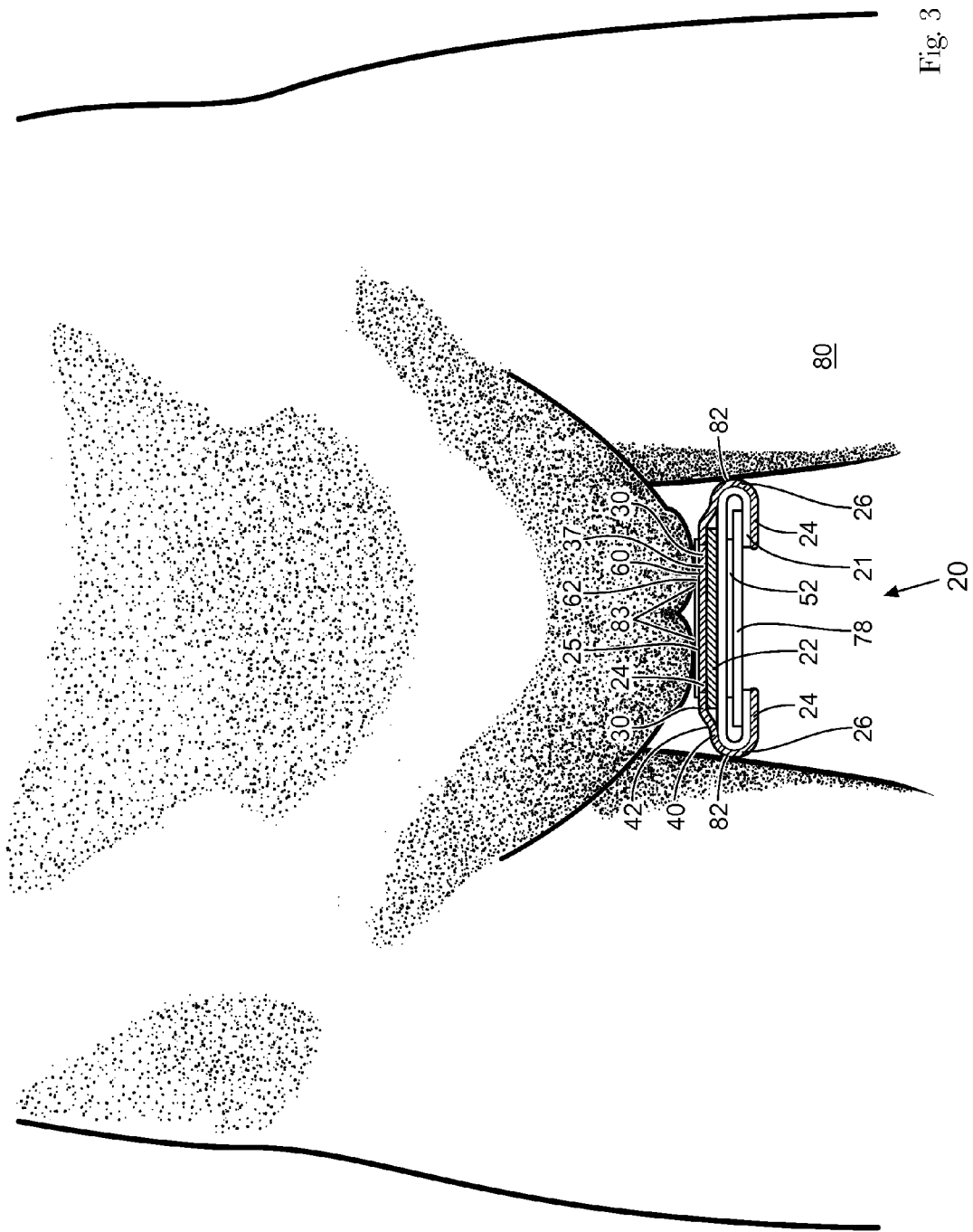
FIG. 3 is an illustration of an absorbent article worn in proximity with a female body.

The topsheet 23 can be thought of as a composite topsheet comprised of a nonwoven 24 and an apertured film 25 that is configured to take advantage of the different properties of each component constituting the topsheet 23. For instance, when the flaps 26 are deployed about the edges of the wearer's undergarment 78 to secure the absorbent article 20 in place, as illustrated in FIG. 3, the apertured film 25 is disposed such that the fluid discharged from the wearer's vagina or urethra is acquired by the absorbent core 22 after the fluid is transported from the wearer's body, past her labia 82, through the apertured film 25, and then through the main body portion 30 of the nonwoven 24. The portions of the nonwoven 24 forming the flaps 26 are folded about the edges of the wearer's undergarment 78 and are positioned such that the nonwoven 24 may contact the inner thigh 82 of the wearer's body 80.

The composite topsheet 23 comprising a nonwoven 24 and apertured film 25 is thought to provide several benefits. Excellent fluid handling characteristics of the topsheet 23 are provided by the apertured film 25. Apertured films are recognized as having fast fluid acquisition rates and minimal rewet. The flaps 26, which wrap around the edges of the wearer's undergarment 78 and can come into contact with the wearer's inner thigh 82, can be comprised of the nonwoven 24. Nonwoven 24 can be of the type that has a soft and cushiony tactile feel. Flaps 26 comprised of a soft and cushiony nonwoven 24 can be comfortable to wear. For instance, in typical absorbent articles worn in the crotch of the wearer, as the wearer walks, the flaps 26 can rub back and forth along the wearer's inner thigh 82, creating the potential for abrasion, chafing, and other irritation of the skin of the wearer's inner thigh 82. Chafing and irritation can create the opportunity for rashes and other skin disorders to develop and result in discomfort to the wearer. Flaps 26 comprised of a soft cushiony nonwoven 24 can be gentler on the skin and reduce the potential for adverse skin conditions to develop as a result of the absorbent article being worn while the wearer is in motion. If the flaps 26 are comprised of a hydrophobic nonwoven, the flaps 26 can resist lateral spreading of the fluid as the fluid passes through the main body portion 30 of the nonwoven 24 as the absorbent article 20 acquires fluid in the core 22. Thus, the flaps 26 can be designed such that they are not readily soiled.

In essence, the nonwoven 24 and apertured film 25, arranged as illustrated in FIG. 1, can provide for an absorbent article with excellent fluid handling characteristics in portions of the absorbent article designed to acquire and retain fluid and flaps 26 that are comfortable to wearer and are not readily soiled by discharge from the wearer's body 80. Flaps 26 comprised of a hydrophobic nonwoven can limit exudates from soiling the edges of the wearer's undergarment. Including a hydrophilic zone 37 in the nonwoven 24 can assist in transporting fluid acquired through the apertured film 25 to the absorbent core 22 and limit the amount of lateral spreading of fluid in the nonwoven 24 to reduce the potential for soiling of the flaps 26 and spreading of the fluid in the plane of the nonwoven 24.

Apertured film 25 can be liquid permeable and, in use, can be in close proximity to the skin of the user. Apertured film 25 can be compliant, soft feeling, and non-irritating to the user's skin. Apertured film 25 can be made from any of the materials conventional for this type of use.

A practical apertured film 25 is described in U.S. Pat. No. 3,929,135, entitled "Absorptive Structure Having Tapered Capillaries", which issued to Thompson on Dec. 30, 1975, U.S. Pat. No. 4,324,426, entitled "Disposable Absorbent Article Having A Stain-Resistant Topsheet", which issued to Mullane and Smith on Apr. 13, 1982, U.S. Pat. No. 4,342,314, entitled "Resilient Plastic Web Exhibiting Fiber-Like Properties", which issued to Radel and Thompson on Aug. 3, 1982, and U.S. Pat. No. 4,463,045, entitled "Macroscopically Expanded Three-Dimensional Plastic Web Exhibiting Non-Glossy Visible Surface and Cloth-Like Tactile Impression", which issued to Ahr, Louis, Mullane, and Ouellette on Jul. 31, 1984. Apertured films 25 can feel dry to the wearer because the apertured film 25 can be non-absorbent yet still be pervious to allow fluids to pass through the apertured film 25. The apertured film sold under the trade name DRI-WEAVE by Procter & Gamble Co. can be employed as the apertured film 25.

A portion or the entire body facing surface of the apertured film 25 can be treated with a surfactant to render the apertured film 25 more hydrophilic. Surfactant can be applied to the apertured film by spraying, padding, or using transfer rolls. The surfactant can reduce the likelihood that fluids will flow off of the surface of the apertured film 25.

The flaps 26 can be from about 5 cm to about 19 centimeters long in a direction generally parallel to the longitudinal centerline L of the main body portion 30 of the nonwoven 24. The flaps 26 can be sized and dimensioned such that the nonwoven 24 is from about 10 cm to about 23 cm wide between the distal edges of the nonwoven 24 in a direction parallel to the transverse centerline T of the nonwoven 24. The flaps 26 can be mirror images of one another and each flap 26 can be symmetric about an axis parallel to the transverse centerline T of the main body portion 30 of nonwoven 24. The flaps can be positioned forward of the transverse centerline T of the main body portion 30 of nonwoven 24 along at least part of the longitudinal side edges 42. The flaps 26 can be separate elements that are joined to the main body portion 30 of nonwoven 24. The flaps 26 can be integral with the main body portion 30 of nonwoven 24, integral meaning that the main body portion 30 and flaps 26 are constituted from the same precursor web or precursor webs. The flaps 26 can extend along less than about eighty percent of the longitudinal side edges 42 of the main body portion 30 of nonwoven 24.

The absorbent core 22 can be compressible, conformable, and non-irritating to the wearer's skin. The absorbent core 22 can be comprised of comminuted wood pulp, which is generally referred to as airfelt, creped cellulose wadding, absorbent foam, absorbent sponges, synthetic staple fibers, polymeric fibers, chitosan, hydrogel-forming polymer gelling agents, peat moss, or any other absorbent material. The absorbent core 22 can comprise polymeric gelling agents in the form of substantially water-insoluble, slightly cross-linked, partially neutralized, hydrogel-forming polymer material.

The absorbent core 22 can have a maximum lateral extent in directions orthogonal to the longitudinal centerline L of the main body portion 30 of nonwoven 24 that is within the longitudinal side edges 42 of the of the main body portion 30 of nonwoven 24. That is, the absorbent core 22 can be laterally inboard of a projection orthogonal to the longitudinal centerline L and transverse centerline T of the longitudinal side edges 42.

The backsheet 21 can be impervious to liquids. Suitable materials for the backsheet 21 can include embossed or non-embossed polyethylene films and laminated tissue. A suitable film for backsheet 21 can be obtained from Monsanto Chemical Corporation and marketed in the trade as Film No. 8020.

Figure 4:
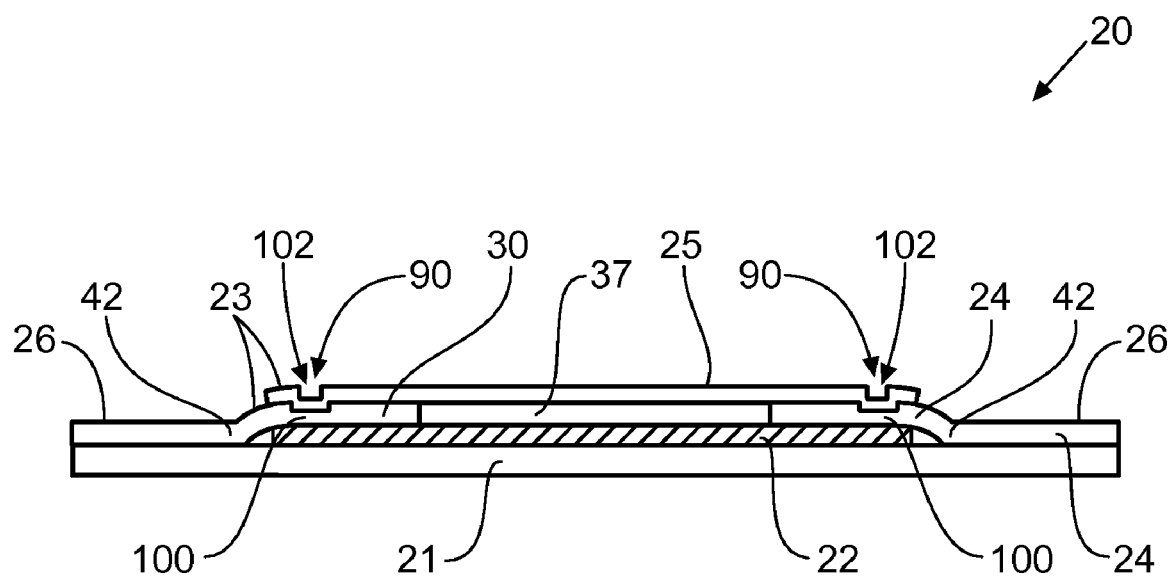
FIG. 4 is an illustration of a cross section of an absorbent article in which the nonwoven has a channel.

The nonwoven 24 can comprise a capillary barrier 100, a non-limiting schematic of which is illustrated in FIG. 4. A capillary barrier 100 can be a portion of the nonwoven 24 that has a fiber density (mass per volume) that is greater than an adjacent portion of the nonwoven. One or more capillary barriers 100 can be arranged such that a capillary barrier 100 lies between the hydrophilic zone 37 and each of the flaps 26. Capillary barrier 100 can be between the longitudinal centerline L and the flaps 26. Each capillary barrier 100 can be between a longitudinal side edge 42 and the longitudinal centerline L. Each capillary barrier 100 can be between the longitudinal side edges 42 of nonwoven 24 and laterally outboard of the hydrophilic zone 37. Capillary barrier 100 can act as a barrier to fluid migration from the hydrophilic zone 37, or portions of the nonwoven 24 proximal the hydrophilic zone 37, to the flaps 26.

A capillary barrier 100 can resist fluid transport across the capillary barrier 100 because of the contrast in partially saturated fluid transport properties of the nonwoven. In general, the matric suction at a given saturation is higher for the part of a nonwoven having a dense arrangement of fibers than for the part of nonwoven having a looser arrangement of fibers because of the smaller average capillary size for the denser part of the nonwoven. The capillary barriers 100 can be arranged such that the capillary barriers are in the main body portion 30 of the nonwoven 24 and lie between the longitudinal centerline L and the longitudinal side edges 42 of nonwoven 24. The capillary barriers 100 can be arranged such that a capillary barrier 100 is between each flap 26 and the hydrophilic zone 37.

A capillary barrier 100 can have the form of a channel 102. Channel 102 can be formed by locally compressing part of the nonwoven 24 to form a densified portion in the nonwoven 24. The densified portion of the nonwoven 24 can be a valley or pinched portion. A channel 102 can generally run (straight or curved or combination of straight and curved portions) in a direction generally parallel to the longitudinal centerline L. A channel 102 can generally run along the length of the nonwoven 24, length being generally aligned with the longitudinal axis L. Channel 102 can be between the longitudinal centerline L and the flaps 26. Channel 102 can be formed in both the apertured film 25 and nonwoven 24, as illustrated in FIG. 4. Channel 102 can be formed only in the nonwoven 24. Channel 102 can be formed in the apertured film 25, nonwoven 24, and absorbent core 22 and can include any other components of the absorbent article 20, such as a secondary topsheet which can be placed between the topsheet 23 and the absorbent core 22, that are in the profile of the absorbent article 20.

Figure 5:
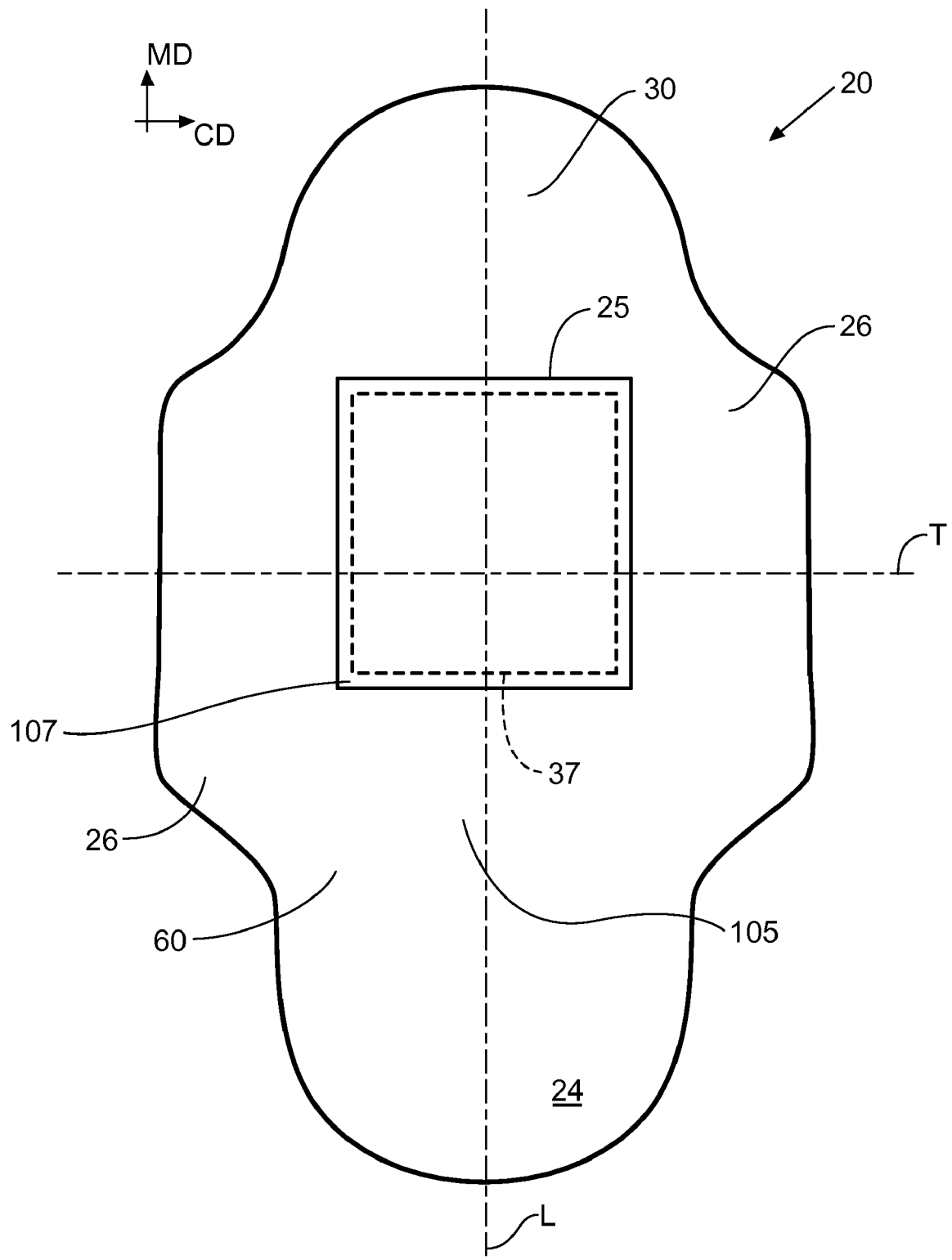
FIG. 5 is a top view of an absorbent article employing a patch of apertured film.

The apertured film 25 can be joined to the nonwoven 24 along the bonding lines 90, the bonding lines 90 being formed by a channel 102 in the apertured film 25 and nonwoven 24. The bonding lines 90 can be formed by locally compressing the apertured film 25 and nonwoven 24 together with one another so that the apertured film 25 and nonwoven 24 become joined and/or releasably joined to one another. The bonding lines 90 can be fusion bonds in which the apertured film 25 and nonwoven 24 are fused together. The bonding lines 90 can comprise a bond selected from the group consisting of an ultrasonic bond, a fusion bond, an adhesive bond, and combinations thereof More than about fifty percent of the apertured film garment facing surface 76 can face the nonwoven body facing surface 60. More than about thirty percent of the nonwoven body facing surface 60 can face the apertured film garment facing surface 76. As shown in FIG. 5, less than the entire body facing surface 60 of the main body portion 30 of nonwoven 24 can be in a facing relationship with the apertured film garment facing surface 76. Less than about seventy-five percent of the nonwoven body facing surface 60 can face the apertured film garment facing surface 76. The apertured film 25 can have a maximum lateral extent within the longitudinal side edges 42 of the main body portion 30 of nonwoven 24. The main body portion 30 of nonwoven 24 can have a main body portion area 105 and the apertured film 25 can have an aperture film area 107. The aperture film area 107 can be less than the main body portion area 105.

Figure 6:
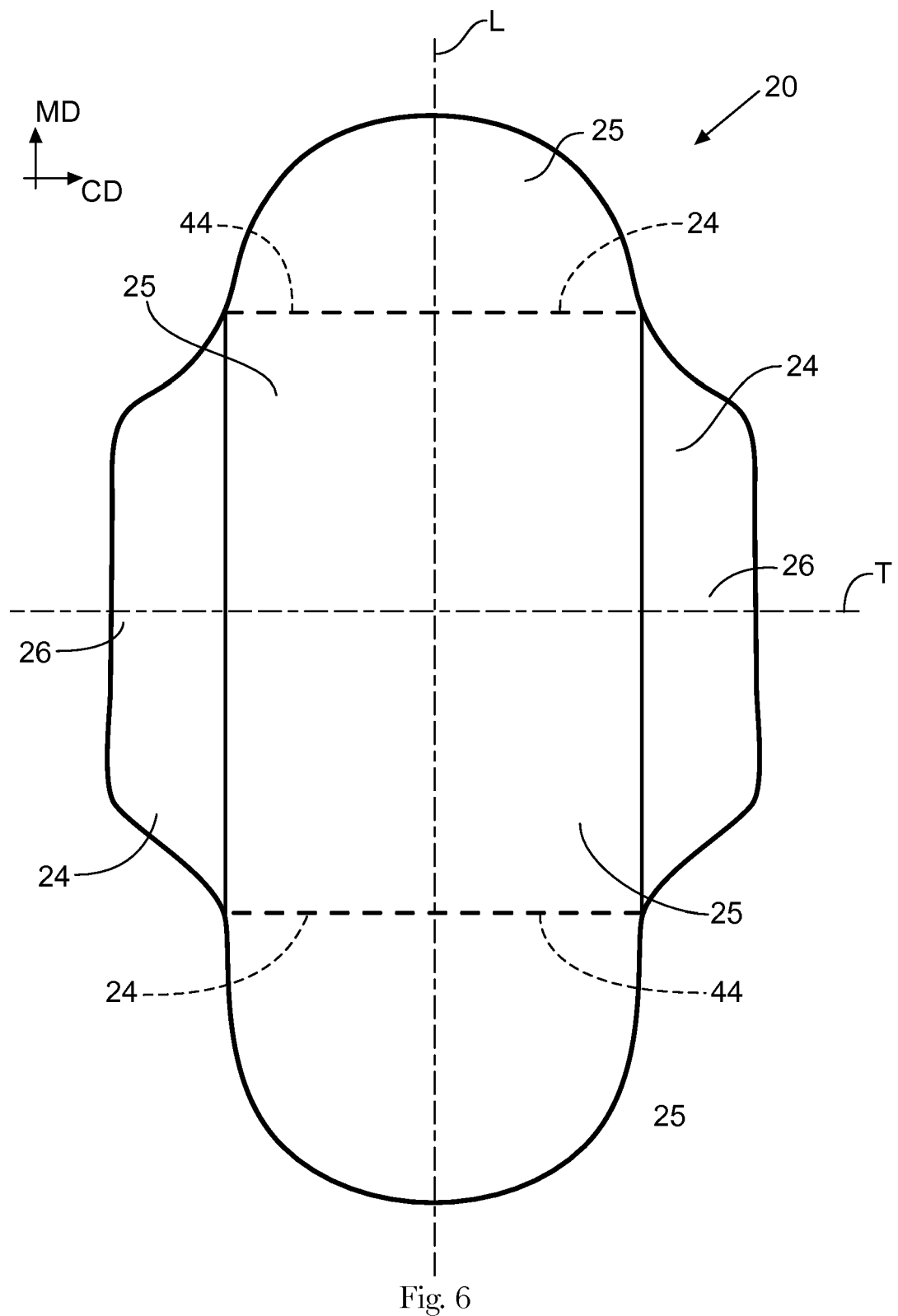
FIG. 6 is a top view of an absorbent article in which the nonwoven does not extend along the entire longitudinal centerline of the absorbent article.

As illustrated in FIG. 6, the nonwoven 24 can extend along less than the entire length of the absorbent article 20, as measured along the longitudinal centerline L. The apertured film 25 can be longer than the nonwoven 24 in a direction measured coincident with the longitudinal centerline L. The apertured film 25 can be shorter than, longer than, or the same length as the nonwoven 24 in a direction measured along the longitudinal centerline L.

The hydrophilic zone 37 can be a zone in which the constituent fibers of the nonwoven 24 are hydrophilic or are rendered to be hydrophilic in some manner. A material can be considered hydrophilic if the material has a static contact angle with water less than 90 degrees or is rendered to have a static contact angle with water less than 90 degrees. A first element can be considered more hydrophilic than a second element if the first element has a static contact angle with water that is less than the static contact angle with water of the second element. The affinity for water, as measured or characterized by contact angle, of a nonwoven can be controlled by selecting the type of fiber or fibers constituting the nonwoven and/or by treating the nonwoven with a substance.

Static contact angle with water for a particular material constituting the nonwoven 24 can be measured by depositing a small drop of water on the nonwoven 24 and measuring the static contact angle between the water and the constituent fibers of the nonwoven 24. Contact angle of the constituent material constituting the nonwoven 24 can be measured on a solid substrate comprised of the same material forming the fibers of the nonwoven 24 and measuring the contact angle of water therewith. For a nonwoven 24 treated with a substance, such as a surfactant, to render the treated zone to be more hydrophilic, contact angle between the fibers of the treated zone of the nonwoven may be measured on a solid substrate comprised of the same material constituting the treated zone of the nonwoven 24 that is also treated with the surfactant.

A zone of nonwoven 24 can be considered a hydrophilic zone 37 if such zone has a static contact angle with water that is less than the static contact angle with water of a portion of the nonwoven 24 outside of such hydrophilic zone 37. The hydrophilic zone 37 can be more hydrophilic as compared to a portion of the flaps 26. The hydrophilic zone 37 can have a static contact angle with water less than 90 degrees and a portion of the remainder of the nonwoven 24 can have a static contact angle with water greater than 90 degrees. In another practical arrangement, the hydrophilic zone 37 can have a static contact angle with water that is less than the static contact angle with water for the nonwoven 24 constituting the flaps 26, both of which have a static contact angle with water less than 90 degrees.

The hydrophilic zone 37 can comprise a substance selected from the group consisting of a non-ionic surfactant, an anionic surfactant, a zwitter-ionic surfactant, and mixtures thereof.

The hydrophilic zone 37 can comprise a non-ionic surfactant. Non-ionic surfactants are thought to be useful because they tend to have relatively low melting temperatures, are relatively easy to process, and tend to be liquid at room temperature as compared to ionic surfactants. Surfactant can be applied to the hydrophilic zone 37 of the nonwoven 24 in an effective amount to render the hydrophilic zone 37 to be hydrophilic or more hydrophilic than the flaps 26. An amount of surfactant applied between about 0.01 gsm and about 100 gsm can be practical. An amount of surfactant applied to the nonwoven 24 between about 0.1 gsm and about 10 gsm can be practical.

The hydrophilic zone 37 of the nonwoven 24 can be treated with a surfactant having a HLB value (hydrophilic to lipophilic balance) between about 3 and about 12. The hydrophilic zone 37 of the nonwoven 24 can be treated with a non-ionic surfactant having a HLB value (hydrophilic to lipophilic balance) between about 3 and about 12. A surfactant having an HLB value between about 6 and about 12 can also be practical for treating the nonwoven 24 to have a hydrophilic zone 37.

A non-ionic surfactant comprising a functional group containing polyether segments can be applied to a portion of the nonwoven 24 to render such portion hydrophilic or more hydrophilic than the flaps 26, thereby forming the hydrophilic zone 37. Nonionic surfactants, including, but not limited to, those comprising functionalities of polyethylene glycol (PEG), polypropylene glycol (PPG), and polybutylene glycol (PBG) functional groups can be used to treat a portion of the nonwoven 24 to form the hydrophilic zone 37. Nonionic surfactants having a functional group selected from the group consisting of polyethylene glycol (PEG), polypropylene glycol (PPG), polybutylene glycol (PBG), and combinations thereof can be used to treat a portion of the nonwoven 24 to form the hydrophilic zone 37. The degree of polymerization of a polyether functional group in a non-ionic surfactant can be between about 2 and about 100.

A non-ionic surfactant comprising a functional group containing polyether segments can be applied to a portion of the nonwoven 24 to render such portion hydrophilic or more hydrophilic than the flaps 26 and anti-fouling or more blood cell resisting than the flaps 26, thereby forming the hydrophilic zone 37. Nonionic surfactants, including but not limited to, those with polyethylene glycol (PEG), polypropylene glycol (PPG), and polybutylene glycol (PBG) functional groups, can be used to treat a portion of the nonwoven 24 to form an anti-fouling hydrophilic zone 37. Nonionic surfactants having functional group selected from the group consisting of polyethylene glycol (PEG), polypropylene glycol (PPG), polybutylene glycol (PBG), and combinations thereof can be used to treat a portion of the nonwoven 24 to form an anti-fouling hydrophilic zone 37.

The hydrophilic zone 37 can comprise a non-ionic surfactant such as ARLAMOL E, available from UNIQEMA, Newcastle, Del., U.S. The International Nomenclature of Cosmetic Ingredients (INCI) for ARLAMOL E is PPG-15 Stearyl Ether. The CAS # of ARLAMOL E is 25231-21-4. The poly (propylene glycol) functionality of ARLAMOL E can have an average degree of polymerization of about 15 with the degree of polymerization ranging from about 8 to about 20. The degree of polymerization of the poly(propylene glycol) functionality of ARLAMOL E can be as low as 3.

The hydrophilic zone 37 can comprise a surfactant that comprises a polypropylene oxide functional group.

Surfactant can be applied to nonwoven 24 in any manner known in the art to apply surfactants to nonwovens including, but not limited to, spraying, padding, using transfer rolls, slot coating, and printing.

In one embodiment, the nonwoven 24 can be a hydrophobic nonwoven such as BBA 28 gsm, lot number BBWW142292, trade name 083YLCCD09P, available from BBA, Washougal Wash., U.S. The hydrophilic zone 37 of the nonwoven can be a zone of the nonwoven 24 in which at least some of the fibers constituting the nonwoven 24 are partially coated or enrobed (i.e. treated) in an surfactant, such as ARLAMOL E. The apertured film 25 can be the apertured film marketed by the Procter & Gamble Co. as DRI-WEAVE.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for wearing in an undergarment, the absorbent article having a body contacting surface and a garment contacting surface, the absorbent article comprising:

a main body portion, said main body portion having a body contacting surface, wherein said main body portion has two spaced apart longitudinal side edges, two spaced apart transverse edges, and a longitudinal centerline, a pair of spaced apart flaps associated with said main body portion, said flaps having a body contacting surface and being sized and dimensioned for folding around and securing to an undergarment, wherein each of said flaps is associated with said main body portion at a juncture, wherein one flap extends laterally outward from each of said longitudinal side edges, a nonwoven extending across said main body portion and said flaps and forming at least a portion of said body contacting surface of said flaps, the nonwoven having a nonwoven body facing surface and a nonwoven garment facing surface, an apertured film forming at least a portion of said body contacting surface of said main body portion, said apertured film having a film body facing surface and a film garment facing surface wherein at least part of said film garment facing surface faces said nonwoven body facing surface;

wherein part of said nonwoven extending across said main body portion comprises a hydrophilic zone that is more hydrophilic than a portion of said nonwoven extending across said flaps.

2. An absorbent article according to claim 1, wherein said absorbent article further comprises an absorbent core, wherein said nonwoven is between said apertured film and said absorbent core.

3. An absorbent article according to claim 2, wherein said absorbent core has a maximum lateral extent within said longitudinal side edges of said main body portion of said nonwoven.

4. An absorbent article according to claim 1, wherein said flaps are integral with said main body portion.

5. An absorbent article according to claim 1, wherein said hydrophilic zone is integral with said main body portion.

6. An absorbent article according to claim 1, wherein said hydrophilic zone comprises a substance selected from the group consisting of a non-ionic surfactant, an ionic surfactant, a zwitter-ionic surfactant, and mixtures thereof.

7. An absorbent article according to claim 1, wherein said hydrophilic zone comprises a non-ionic surfactant.

8. An absorbent article according to claim 7, wherein said non-ionic surfactant is applied at a surface density of about 0.1 grams per square meter to about 10 grams per square meter.

9. An absorbent article according to claim 7, wherein said non-ionic surfactant has an HLB value between about 3 and about 14.

10. An absorbent article according to claim 9, wherein said non-ionic surfactant comprises a functional group containing polyether segments.

11. An absorbent article according to claim 10 wherein said functional group containing polyether segments has a degree of polymerization between about 2 and about 100.

12. An absorbent article according to claim 9 wherein said non-ionic surfactant comprises a functional group containing polypropylene oxide.

13. An absorbent article according to claim 1, wherein said apertured film is joined to said nonwoven by a bond selected from the group consisting of an ultrasonic bond, a fusion bond, an adhesive bond, and combinations thereof.

14. An absorbent article according to claim 1, wherein portions of said nonwoven between said hydrophilic zone and said flaps are less hydrophilic than said hydrophilic zone.

15. An absorbent article according to claim 1, wherein said film is joined to said nonwoven along a pair of bonding lines, wherein a bonding line is between said hydrophilic zone and each of said flaps.

16. An absorbent article according to claim 1, wherein said nonwoven comprises a capillary barrier, said capillary barrier defined by a portion of said nonwoven having a density of fibers that is greater than that for an adjacent portion of said nonwoven.

17. An absorbent article according to claim 16, wherein said capillary barrier has a form of a channel.

18. An absorbent article according to claim 1, wherein said nonwoven comprises a capillary barrier, said capillary barrier defined by a portion of said nonwoven having a density of fibers that is greater than that an adjacent portion of said nonwoven, wherein said capillary barrier is between said hydrophilic zone and one of said flaps.

19. An absorbent article according to claim 1, wherein said main body portion of said nonwoven has a main body portion area and said film has a film area, wherein said film area is less than said main body portion area.

20. An absorbent article according to claim 1, wherein said nonwoven comprises a pair of fusion barriers, said fusion barriers disposed on opposing sides of said longitudinal centerline, wherein a fusion barrier is between said longitudinal centerline and each of said flaps.

* * * * *